United States Patent [19]

Chu et al.

[11] Patent Number: 4,916,122
[45] Date of Patent: Apr. 10, 1990

[54] 3'-AZIDO-2',3'-DIDEOXYURIDINE ANTI-RETROVIRAL COMPOSITION

[75] Inventors: Chung K. Chu, Athens; Raymond F. Schinazi, Tucker, both of Ga.

[73] Assignees: University of Georgia Research Foundation, Inc., Athens; Emory University, Atlanta, both of Ga.

[21] Appl. No.: 104,438

[22] Filed: Oct. 2, 1987

Related U.S. Application Data

[63] Continuation-in-part of Ser. No. 7,473, Jan. 28, 1987.

[51] Int. Cl.$^4$ ............................................. A61K 31/70
[52] U.S. Cl. ........................................ 514/50; 514/51
[58] Field of Search ...................... 536/23; 514/50, 51

[56] References Cited

U.S. PATENT DOCUMENTS

| | | | |
|---|---|---|---|
| 3,282,921 | 11/1969 | Verheyden et al. | 536/23 |
| 3,687,931 | 8/1972 | Verheyden et al. | 536/26 |
| 3,755,295 | 8/1973 | Verheyden et al. | 536/23 |
| 3,775,397 | 11/1973 | Etzold et al. | 536/23 |
| 3,817,982 | 6/1974 | Verheyden et al. | 536/23 |
| 4,071,680 | 1/1978 | Cook | 536/23 |
| 4,093,715 | 6/1978 | Lin et al. | 536/23 |
| 4,128,639 | 12/1978 | Lin et al. | 536/23 |

(List continued on next page.)

FOREIGN PATENT DOCUMENTS

| | | |
|---|---|---|
| 86253146.39 | 10/1986 | European Pat. Off. |
| 86301897.4 | 10/1986 | European Pat. Off. |
| 86307071.0 | 4/1987 | European Pat. Off. |
| 224490 | 7/1985 | Fed. Rep. of Germany |
| 3608606A1 | 9/1986 | Fed. Rep. of Germany |
| 3608606.1 | 9/1986 | Fed. Rep. of Germany |
| 8506868 | 3/1985 | United Kingdom |
| 8506869 | 3/1985 | United Kingdom |

(List continued on next page.)

OTHER PUBLICATIONS

De Clercq et al., Pharm. 97, 174446t (1982).
Busson, et al., Chem. Abstracts 96, 69346s (1982).
Nth. App. 81 00, 177 Chem. Abstracts 98, 4753u (1983).
Krenitsky, et al., J. Med. Chem. 26(6) 891–896 (1983).
Lin et al., J. Med. Chem. 26, 544–548 (1983).
Lin, et al., J. Med. Chem. 26, 1691–1696 (1983).
Laitseva, et al., Carbohydrates 101, 192378c (1984).
Fox, et al., Herpes Viruses and Virus Chemotherapy Elsevier Science Publishers B.V. (Biomedical Division) 53–56 (1985).
Colla, et al., Eur. J. Med. Chem.—Chim. Ther. 20(4) 295–301 (1985).
Schinazi, et al., Antimicrobial Agents and Chemotherapy 28(4), 552–560 (1985).
Brubaker, et al., Chem. Abstracts 102: 226110x (1985).

*Primary Examiner*—John W. Rollins
*Attorney, Agent, or Firm*—Kilpatrick & Cody

[57] ABSTRACT

Compositions for the treatment of AIDS and ARC having the following compound as an active ingredient:

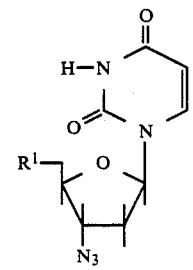

where $R^1$ is OH, monophosphate, diphosphate, or triphosphate; or a pharmacologically acceptable salt thereof.

The primary advantage of this compound is its highly selective anti-retroviral activity, i.e., it significantly decreases viral replication as measured as reverse transcriptase activity while demonstrating orders of magnitude less cytotoxicity than other anti-viral compounds such as AZT.

In a preferred embodiment, the compound is present in an amount sufficient to inhibit the HIV reverse transcriptase activity but not significantly inhibit human DNA polymerase activity. Also included within the scope of this invention are 3'-azido-2',3'-dideoxyuridine mono-, di-, and triphosphate and compositions containing these compounds as the active agent.

6 Claims, 6 Drawing Sheets

U.S. PATENT DOCUMENTS

| | | | |
|---|---|---|---|
| 4,210,638 | 7/1980 | Greer | 514/49 |
| 4,230,698 | 10/1980 | Bobek et al. | 536/24 |
| 4,331,662 | 8/1982 | Eckstein et al. | 514/49 |
| 4,522,811 | 6/1985 | Eppstein et al. | 514/2 |
| 4,540,566 | 9/1985 | Davis et al. | 424/480 |
| 4,604,382 | 8/1989 | Lin et al. | 536/23 |
| 4,710,492 | 12/1987 | Lin et al. | 514/50 |
| 4,724,232 | 2/1981 | Rideout et al. | 514/51 |
| 4,780,453 | 10/1988 | Rideout et al. | 514/50 |

FOREIGN PATENT DOCUMENTS

| | | |
|---|---|---|
| 8511774 | 3/1985 | United Kingdom . |
| 8511775 | 3/1985 | United Kingdom . |
| 8523878 | 9/1985 | United Kingdom . |
| 8523881 | 9/1985 | United Kingdom . |
| 8603719 | 12/1985 | United Kingdom . |
| 8603447 | 1/1986 | United Kingdom . |
| 8603450 | 1/1986 | United Kingdom . |
| 8615322 | 5/1986 | United Kingdom . |
| 8608272 | 9/1986 | United Kingdom . |

Relative effect of AzT, CS-85 and CS-87 on colony formation of human granulocytes-macrophage precursor cells.

Effect of CS-87 on the growth of Vero cells
(measured on day 3)

Effect of CS-87 on the growth of human PBM cells
(measured on day 5)

Effect of CS-85 and CS-87 on the weight of uninfected BALB/c mice. Mice treated intraperitoneally with 60mg/kg per day (BID 6d)

Effect of CS-85 and CS-87 on liver enzymes in rhesus monkeys

Effect of CS-85 and CS-87 on liver enzymes in rhesus monkeys

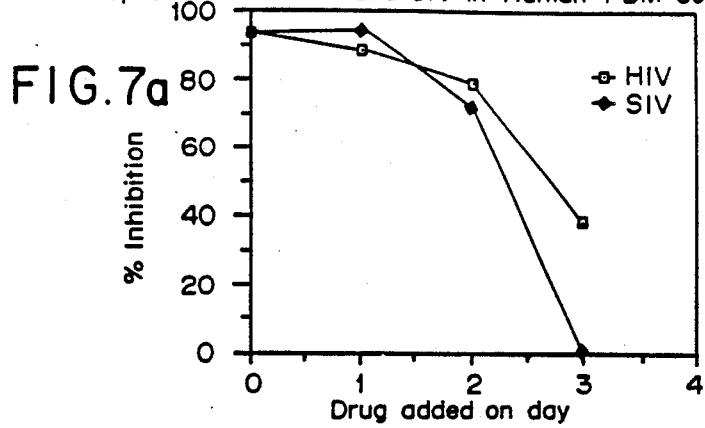
FIG. 7a — Effect of Delayed Treatment with AZT (0.1 uM) on the Replication of HIV-1 and SIV in Human PBM Cells
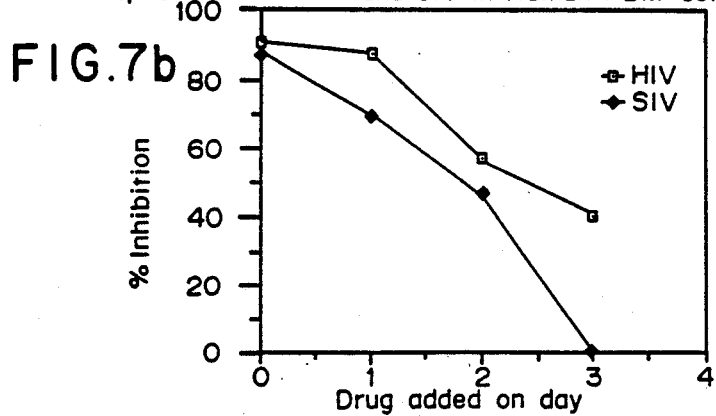
FIG. 7b — Effect of Delayed Treatment with CS-87 (10 uM) on the Replication of HIV-1 and SIV in Human PBM Cells
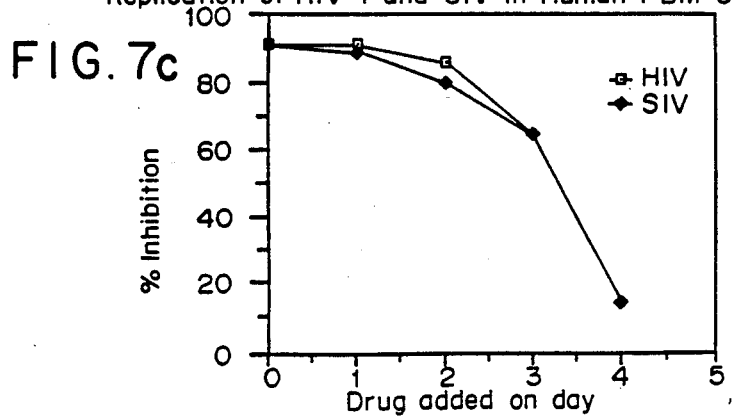
FIG. 7c — Effect of Delayed Treatment with CS-91 (10 uM) on the Replication of HIV-1 and SIV in Human PBM Cells

3'-AZIDO-2',3'-DIDEOXYURIDINE ANTI-RETROVIRAL COMPOSITION

The U.S. Government has rights in this invention as a result of the investigations leading to this invention being funded in part by a VA Merit Review Award.

This is a continuation-in-part of U.S. Ser. No. 007,473 entitled "3'-Azido-2',3'-Dideoxypyrimidines and Related Compounds as Antiviral Agents" filed Jan. 28, 1987 by Chung K. Chu and Raymond F. Schinazi.

BACKGROUND OF THE INVENTION

The present invention relates to 3'-azido-2',3'-dideoxyuridine (referred to as CS-87 herein) and compositions thereof as agents for the prevention and treatment of retroviral diseases, particularly human acquired immunodeficiency (AIDS) virus (HIV-1; and also known as HTLV-III/LAV), which causes acquired immunodeficiency syndrome (AIDS).

BRIEF DESCRIPTION OF THE BACKGROUND

AIDS was recognized as early as 1979. The number of cases reported to the Centers for Disease Control (CDC) has increased dramatically each year since then, and in 1982 the CDC declared AIDS a new epidemic. AIDS is generally accepted at this time to be a consequence of infection with the retrovirus variously termed human T-lymphotropic virus type III (HTLV-III), lymphadenopathy-associated virus (LAV), AIDS associated retrovirus (ARV), or human immunodeficiency virus (HIV-1). Antibodies of these viruses are present in over 80% of patients diagnosed as having AIDS or pre-AIDS syndrome, and have been found with high frequency in the identified risk groups.

There is considerable difficulty in diagnosing the risk of development of AIDS. AIDS is known to develop in at least 10% of the individuals infected with HIV, although this percentage is suspected to be much higher.

A patient is generally diagnosed as having AIDS when a previously healthy adult with an intact immune system acquires impaired T-cell immunity. The impaired immunity usually appears over a period of eighteen months to three years. As a result of this impaired immunity, the patient becomes susceptible to opportunistic infections, various types of cancer such as Kaposi's sarcoma, and other disorders associated with reduced functioning of the immune system.

Another condition associated with HIV is AIDS-related complex, or ARC. This condition is thought to lead eventually to AIDS.

No treatment capable of preventing or reversing the immunodeficiency of AIDS or ARC is currently available. All patients with opportunistic infections and approximately half of all patients with Kaposi's sarcoma have died within two years of diagnosis. Attempts at reviving the immune systems in patients with AIDS have been unsuccessful.

A number of compounds have demonstrated antiviral activity against this virus which include HPA-23, interferons, ribavirin, phosphonoformate, ansamycin, suramin, imuthiol, penicillamine, rifabutin, AL-721, 3'-azido-3'-deoxythymidine (AZT), and other 2',3'-dideoxynucleosides.

AZT appears to be the drug of choice at this time. However, preliminary results indicate that AZT exhibits toxicity in a clinical setting. See Yarchoan et al., Lancet 575-580 (1986). AZT was originally synthesized by Horwitz et al., J. Org. Chem. 29, 2076-2078, 1974. Its activity against Friend Leukemia virus (a retrovirus) was reported as early as 1973 (see Ostertag et al., Proc. Natl. Acad. Sci. USA 71, 4980-4985 (1974); Krieg et al., Exptl. Cell. Res. 116, 21-29, 1978 and references cited therein).

In general, inhibitors of cellular processes will often limit viral replication, but such agents are usually quite toxic for the host as well. Most of the antiviral drugs that have been discovered so far cannot be prescribed for a prolonged period of time because of their toxicity. For example, a compound structurally related to the compounds of the present invention, idoxuridine, is limited in clinical usefulness to topical application in ophthalmic solutions for treatment of herpetic keratitis because of its toxicity to normal cells. Clearly, there is a strong demand for new antiviral agents of low toxicity.

CS-87 is a known compound. See, for example, Lin et al., J. Med. Chem. 26, 1691-1696 (1983), Lin and Mancini, J. Med. Chem. 26, 544-548, Colla et al., Eur. J. Med. Chem.—Chim. Ther. 295-301 (1985).

Lin et al. tested the activity of both CS-87 and DDC against L1210 and sarcoma 180 cells in vitro and found that both of these compounds are inactive against both cell lines. Lin et al. also report that both CS-87 and DDC exhibit only marginal inhibitory activity towards two particular enzymes isolated from L1210 cells. Lin et al. do not disclose a composition containing these compounds in a low concentration sufficient to inhibit replication of HIV or even that these compounds could be used to treat HIV.

Lin and Mancini report that CS-87 and DDC are both inactive against L1210 cells. No other activity for these compounds is reported.

Colla et al. report that CS-87 is inactive against a variety of viruses. In particular, Colla et al. report that CS-87 is inactive against Coxsackie virus B4, polio virus-1, reovirus-1, parainfluenza virus-3, Sindbis virus and measles. Colla et al. thus conclude that azido derivatives such as CS-87 do not have significant antiviral activity.

In light of the state of the art, it is clear that there remains a strong need for new antiviral agents, especially those with low toxicity to normal cells. More particularly, because of the high mortality of AIDS and the lack of an effective treatment for this disease, there remains a great need for development of new low toxicity agents for such treatment because AIDS patients require a long term therapy, possibly an entire life span. It was in this context that the present invention was achieved.

It is therefore an object of the present invention to provide new antiviral compositions having low toxicity towards uninfected cells.

It is a further object of this invention to provide compositions for inhibiting the growth of HIV.

It is yet another object of the present invention to provide a method for the prevention and treatment of infection by HIV.

SUMMARY OF THE INVENTION

These and other objects of the invention, which will hereinafter become more readily apparent, have been obtained by providing compositions having the following compound as an active ingredient:

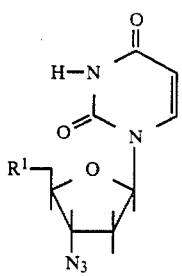

where $R^1$ is OH, monophosphate, diphosphate, or triphosphate; or a pharmacologically acceptable salt thereof.

The primary advantage of this compound is its highly selective anti-retroviral activity, i.e., it significantly decreases viral replication as measured as reverse transcriptase activity while demonstrating orders of magnitude less cytotoxicity than other anti-viral compounds such as AZT.

This compound is provided as an active ingredient in compositions suitable for administration to a patient and are contained therein in an amount sufficient to exhibit in vitro or in vivo activity against HIV. In a preferred embodiment, the compound is present in an amount sufficient to inhibit the HIV reverse transcriptase activity but not significantly inhibit human DNA polymerase activity. Also included within the scope of this invention are 3'-azido-2',3'-dideoxyuridine mono-, di-, and triphosphate and compositions containing these compounds as the active agent.

Also encompassed by the present invention is a method of prevention or treatment of AIDS or ARC, which involves administering a composition containing the above compound to a person infected with HIV or at risk of acquiring the virus. Administration of the drug may be accomplished orally, in a controlled release device or in combination with a liposome delivery system, by injection, or other means known to those in the art, alone or in combination with other active agents.

BRIEF DESCRIPTION OF THE DRAWINGS

FIGS. 7a, b, and c are graphs of the effect of delayed treatment with AZT (a), CS-87 (b), and CS-91 (3' azido 2',3'-dideoxycytidine (c) in human PBM cells as percent inhibition versus day drug administered.

DESCRIPTION OF THE PREFERRED EMBODIMENTS

Figure 1:
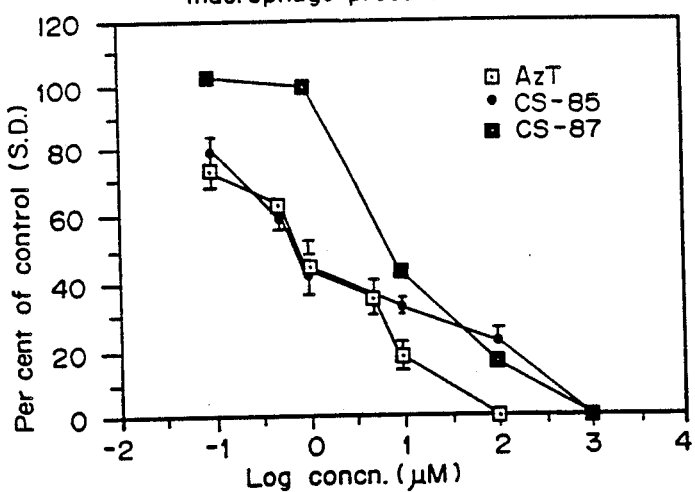
FIG. 1 is a graph showng the relative effects of AZT, CS-85 (3'-azido-2',3'-dideoxy-5-ethyl-uridine) and CS-87 on colony formation of human granulocyte-macrophage precursor cells.

The present invention is based on the discovery that 3'-azido-2',3'-dideoxyuridine (CS-87) and acylated and phosphorylated derivatives thereof exert a highly selective antiviral activity against HIV while, at the same time, exhibiting remarkably low toxicity towards normal cells. Although CS-87 is a known compound per se, it has not hitherto been known that this compound could exert potent antiviral activity against HIV, and, accordingly, compositions containing this compound in the low concentrations sufficient to exert such activity against HIV with minimal side effects have been unknown. Previously, various workers have reported that CS-87 has very little or no activity against both a wide variety of viruses and against certain tumor cells. Due to the low or non-existent activity, relatively concentrated solutions of this compound were utilized, but even these compositions did not result in significant activity.

It has now been discovered that the 50% effective dose ($EC_{50}$) in cell culture of CS-87 against HIV is less than 1 micromolar, more precisely, 200 nanomolar, even taking into consideration that the effective dose and relative toxicity of the compound vary according to the cell type. The relative non-toxicity of the compound has been demonstrated both in cell culture and in animals, including mice and monkeys. Although CS-87 and related compounds exhibit reduced toxicity to normal cells (see Figures and Biological Data Section below), administration of a high concentration of such a drug would nevertheless produce some adverse side effects. By high concentration is meant a dosage which would result in a blood serum concentration of approximately 100 $\mu$M or higher. Thus, compositions having a high concentration of the active ingredient are not considered to be therapeutically effective.

Although AZT is somewhat more active than CS-87 against HIV, CS-87 has a similar therapeutic index when tested in the same type of cell cultures. The therapeutic index of a compound is determined by dividing the inhibitory or lethal dose for 50% of the population ($IC_{50}$ or $LD_{50}$) by the effective dose for 50% if the population ($EC_{50}$).

The discovery that the present compounds are active against HIV at low concentrations and at the same time quite low in toxicity to normal host cells at the lower concentration was surprising, since a known compound of close structural similarity which is presently in clinical trials, AZT, exhibits a much greater toxicity as measured by various experiments. The results reported in FIG. 1 clearly show a significant difference in the effect of CS-87 on colony formation of human granulocytes-macrophage precursor cells in comparison to AzT. It should be noted that CS-87 appears to exert even lower toxicity towards these cells than Cs-85, which is the subject of patent application U.S. Ser. No. 857,947, filed May 1, 1986 by the same inventors, now U.S. Pat. No. 4,681,933, which is hereby incorporated by reference herein.

As used in this invention, antiviral activity refers to the ability of a composition to inhibit the growth of HIV. The claimed composition also exhibits antiviral activity towards other retroviruses.

The ability of the present compositions to inhibit HIV may be measured by various experimental techniques. One such technique involves the inhibition of viral replication in human peripheral blood mononuclear cells. The amount of virus produced is determined by measuring the virus-coded reverse transcriptase (an enzyme found in retroviruses). Results with this assay are illustrated in Table 3 (see Biological Data section herein) and described further in the experimental examples below. Other assays are described as follows.

METHODS

Antiviral Assays

Evaluation in phytohemagglutinin (PHA)-stimulated human peripheral blood mononuclear (PBM) cells infected with HIV-1 (strain LAV)

A. PBM ($2 \times 10^6$ cells/ml; volume 5 ml) from a healthy individual that have been cultured for 3-4 days after PHA stimulation are placed in a 25 cm$^2$ flask in duplicate.

B. The medium, with the drug (2 times the final concentration) or without drug is then added to the flasks (5 ml; final volume 10 ml). AZT is included as a positive control.

C. The cells are exposed to the virus (about 10,000 counts/ml, as determined by reverse transcriptase assay) and are then placed in a $CO_2$ incubator. HIV-1 (strain LAV) is obtained from the Centers for Disease Control, Atlanta, Ga. The RT levels of stock virus is usually over $10^6$ cpm RT/ml. Similar results are obtained when Step C is performed before step B.

D. On day 5, the cells and supernatant are transferred to a 15 ml tube and centrifuged at about 900 g for 10 minutes. Five ml of supernatant are removed and the virus is concentrated by centrifugation at 40,000 rpm for 30 minutes (Beckman 70.1 Ti rotor). The solubilized virus pellet is processed for determination of the levels of reverse transcriptase. Results are expressed in dpm/ml of sampled supernatant.

This experiment shows that CS-87 has significant activity in inhibiting replication of HIV in vitro.

Evaluation in ATH-8 cells infected with HIV-1 (Strain HTLV-III)

CS-87 was screened for its antiviral activity on ATH-8 cells (S. Broder et al., NCI/NIH, Bethesda, Md.). ATH-8 cells are first treated with polybrene (2 g/ml in growth medium) for 30 minutes at 37° C. The cells are then collected by gentle centrifugation (40 g for 15 minutes at 4° C.) and resuspended in clarified (8,000 g for 15 minutes at 4° C.) two day old supernatant obtained from H9/HTLVIII$_B$ infected cells. Following a 60 minute adsorption period at 37° C., the cells are dispensed into the U-bottom wells of 96-well trays ($2 \times 10^4$ cells in 0.1 ml per well). An equal volume (0.1 ml) of supplemented RPMI 1640 medium containing test compound and twice the normal concentration of interleukin-2 is then added to each well.

Test compounds are evaluated at seven half-log dilutions, ranging from 100 to 0.1 μg/ml. Triplicate virus-infected cultures and one uninfected compound cytotoxicity control culture are included at each dosage level. Cultures are incubated at 37° C. in a humidified atmosphere of 5% $CO_2$-95% air incubator. The sizes of the cell pellets in the test compound wells are compared to the pellet sizes of infected and uninfected cell control wells daily for 10 days. On day 10 after infection aliquots are taken from individual wells and the total cell number and cell viability (based on trypan-blue dye exclusion) are determined. 2',3'-Dideoxycytidine and AZT are included as positive controls.

Evaluation in Hela-T4 cells infected with HIV-1 (Strain RF-II)

HeLa-T4 cells (described in Cell 47: 333, 1986) are maintained in Dulbecco's Modified Eagle medium containing 10% inactivated fetal calf serum, penicillin (100 U/ml) and streptomycin (100 μg/ml), and the antibiotic G418 (1 mg/ml). The cells are seeded onto a 96-well plate ($2 \times 10^4$ cells/well per 0.1 ml), and two days later, the supernatant is removed and the virus added. After adsorption for 45 minutes, the inoculum is removed and the cells washed with phosphate-buffered saline (pH 7.2). The compounds at different concentration are then added in maintenance medium (containing 2% serum). The plates are incubated in a 5% $CO_2$-95% air incubator (humidified) and the syncytia allowed to develop for 48 hours before fixation. The cells are fixed with a mixture of 5% glacial acetic acid/95% Ethanol for 15 minutes, and then stained with Giemsa (20% in PSB) for 4 hours. The plates are then washed and dried. The foci are then enumerated with a dissecting stereomicroscope.

p24 RIA procedure

Cell-free culture supernatant is adjusted to 0.5% Triton X-100 prior to determination of the HIV-1 p24 levels using a DuPont RIA kit. A standard curve is generated over the range of 0.625 to 20 ng/ml p24 using partially purified inactivated viral lysate (calibrated against purified p24). The lower limit of sensitivity for this assay is 30 pg/ml of p24.

Western blot analyses

The viral pellet is dissolved in 2.5 mM Tris buffer (pH 8.0) containing 1% SDS, 50 mM DTT, and tracking dye and subjected to a western blot analysis by a technique similar to that described by Burnette in *Anal. Biochem.* 112, 195-203 (1981). A well defined antiserum obtained from an AIDS patient is used to detect the separated proteins. The intensity of the bands is determined semiquantitatively (visually) or with a laser densitometer.

The compounds of this invention have the following structure:

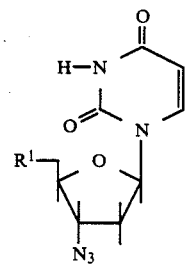

where R$^1$ is OH, monophosphate, diphosphate, or triphosphate; or a pharmacologically acceptable salt thereof, in association with a pharmaceutically acceptable carrier.

The compounds included in the present invention may also be in the form of salts such as, for example, potassium, sodium, and quaternary amine salts, etc. Lyxo analogs of the present compounds are also encompassed within the scope of this invention. For example, the 3' substituent may have the opposite configuration from that shown in the figure.

The compounds of this invention may be synthesized by methods known in the art. Lin et al, Colla et al, and Lin and Mancini, discussed above, each provide synthetic procedures which may be used to prepare these compounds. A specific method of synthesis leading to CS-87 is as follows.

5'-O-Trityl-2'-deoxyuridine(2)

A solution of (50 g, 0.22 mole) of 2'-deoxyuridine and 62 g (0.22 mole) of trityl chloride in 350 ml of dry pyridine is placed in a preheated (100° C.) flask and stirred at 100° C. under air condenser for two hours. The reaction mixture was cooled to room temperature and slowly poured into 4 L of vigorously stirred ice-water. The solid obtained was filtered, washed with water until free from pyridine, and dissolved in chloroform and dried ($Na_2SO_4$ or $MgSO_4$). Filtration and evaporation of chloroform yielded the product as an syrup (96 g, 93%), which was used for the next reaction without further purification.

3'-O-Mesyl-5'-trityl-2'-deoxyuridine(3)

To an ice-cooled solution of 2 (96 g, 0.2 mol) in 350 ml of dry pyridine added dropwise 70 ml of mesyl chloride (98%, sp. gr. 1480). The mixture was stirred in ice-water bath for 3 hours and poured slowly into vigorously stirred ice-water. The solid precipitated was filtered, washed with water and dried (101 g, 94%).

2,3'-Anhydro-5'-O-trityl-2'-deoxyuridine(4)

3'-O-Mesyl-5'-O-trityl-2'-deoxyuridine (101 g, 0.19 mol) was suspended in 350 ml of ethanol (95%) and the mixture was heated to reflux. To the refluxing mixture added dropwise 125 ml of an aqueous solution of sodium hydroxide (2N). The reaction mixture was concentrated under vacuum. The syrupy residue was purified by flash vacuum chromatography over a silica gel column eluting sequentially with chloroform, chloroform-methanol (50:1) and finally with chloroform-methanol (30:1). Evaporation of the pure fractions yielded 72 g (88%) of white powder.

3'-Azido-5'-O-trityl-2',3'-dideoxyuridine(5)

A mixture of 4 (72 g, 0.165 mol) and 50 g of lithium azide in 250 ml of dry dimethylformamide was heated at 110°-120° C. for 12 hours. The reaction mixture was cooled and slowly poured into 4 L of ice-water. The solid obtained was filtered, washed with water, and dissolved in chloroform and dried ($MgSO_4$). Filtration and evaporation of chloroform yielded 63 g (80%) of the product as a syrup.

3'-Azido-2',3'-dideoxyuridine (CS-87)(6)

A mixture of 3'-azido-5'-O-trityl-2',3'-dideoxyuridine(5) (63 g, 0.132 mol) and 300 ml of acetic acid (80%) was heated at 95°-100° C. for two hours. The reaction mixture was cooled in an ice-bath and the solid separated was filtered off. The filtrate was evaporated to dryness. The residue was dissolved in a methanol-chloroform mixture and concentrated to a syrup. The purification of the residue by flash vacuum chromatography over a silica gel column eluting sequentially with chloroform-methanol (70:1), chloroform-methanol (50:1) and finally chloroform-methanol (30:1) yielded 23 g (70%) of colorless product.

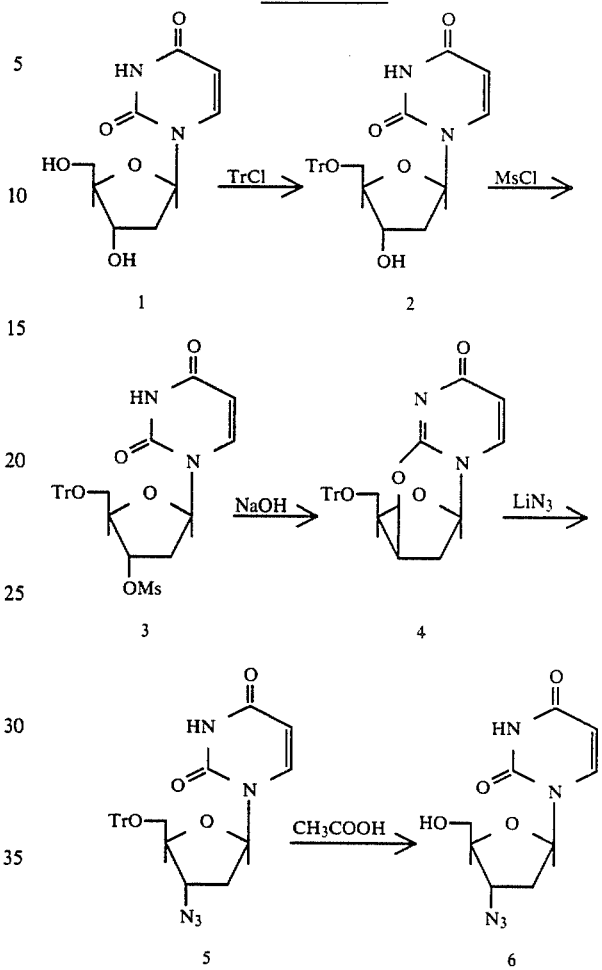

SYNTHESIS

Humans suffering from diseases caused by HIV can be treated by administering to the patient a pharmaceutically effective amount of CS-87 in the presence of a pharmaceutically acceptable carrier or diluent. A preferred carrier/diluent for oral administration is water, especially sterilized water. If administered intravenously, preferred carrier/diluents are physiological saline or phosphate buffered saline (PBS). The compounds according to the present invention are included in the pharmaceutically acceptable carrier or diluent in an amount sufficient to exert a therapeutically useful inhibitory effect on HIV in vivo without exhibiting adverse toxic effects on the patient treated. By "HIV inhibitory amount" is meant an amount of active ingredient sufficient to exert an HIV inhibitory effect as measured by, for example, an assay such as the ones described herein.

There may also be included as part of the composition pharmaceutically compatible binding agents, and-/or adjuvant materials. The active materials can also be mixed with other active materials which do not impair the desired action and/or supplement the desired action. The active materials according to the present invention can be administered by any route, for example, orally, parenterally, intravenously, intradermally, subcutaneously, or topically, in liquid or solid form.

A preferred mode of administration of the compounds of this invention is oral. Oral compositions will generally include an inert diluent or an edible carrier. They may be enclosed in gelatin capsules or compressed into tablets. For the purpose of oral therapeutic administration, the aforesaid compounds may be incorporated with exipients and used in the form of tablets, troches, capsules, elixirs, suspensions, syrups, wafers, chewing gums and the like. These preparations should produce a serum concentration of active ingredient of from about 0.2 to 40 $\mu$M. A preferred concentration range is from 0.2 to 20 $\mu$M and most preferably about 1 to 10 $\mu$M. However, the concentration of active ingredient in the drug composition itself will depend on bioavailability of the drug and other factors known to those of skill in the art.

It is to be noted that dosage values will also vary with the specific severity of the disease condition to be alleviated. It is to be further understood that for any particular subject, specific dosage regimens should be adjusted to the individual need and the professional judgment of the person administering or supervising the administration of the aforesaid compositions. It is to be further understood that the concentration ranges set forth herein are exemplary only and they do not limit the scope or practice of the invention. The active ingredient may be administered at once, or may be divided into a number of smaller doses to be administered at varying intervals of time.

The tablets, pills, capsules, troches and the like may contain the following ingredients: a binder such as microcrystalline cellulose, gum tragacanth or gelatin; an excipient such as starch or lactose, a disintegrating agent such as alginic acid, Primogel, corn starch and the like; a lubricant such as magnesium stearate or Sterotes; a glidant such as colloidal silicon dioxide; and a sweetening agent such as sucrose or saccharin or flavoring agent such as peppermint, methyl salicylate, or orange flavoring may be added. When the dosage unit form is a capsule, it may contain, in addition to material of the above type, a liquid carrier such as a fatty oil. Other dosage unit forms may contain other various materials which modify the physical form of the dosage unit, for example, as coatings. Thus tablets or pills may be coated with sugar, shellac, or other enteric coating agents. A syrup may contain, in addition to the active compounds, sucrose as a sweetening agent and certain preservatives, dyes and colorings and flavors. Materials used in preparing these various compositions should be pharmaceutically pure and non-toxic in the amounts used.

The solutions or suspensions may also include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parental preparation can be enclosed in ampoules, disposable syringes or multiple dose vials made of glass or plastic.

The compositions of the present invention are prepared as formulations with pharmaceutically acceptable carriers. Preferred are those carriers that will protect the active compound against rapid elimination from the body, such as a controlled release formulation, including implants and microencapsulated delivery systems. Biodegradable, biocompatible polymers can be used, such as polyanhydrides, polyglycolic acid, collagen, and polylactic acid. Methods for preparation of such formulations will be apparent to those skilled in the art.

Liposomal suspensions (including liposomes targeted to infected cells with monoclonal antibodies to viral antigens) are also preferred as pharmaceutically acceptable carriers. These may be prepared according to meethods known to those skilled in the art, for example, as described in U.S. Pat. No. 4,522,811 (the pertinent portions of which are incorporated herein by reference). For example, liposome formulations may be prepared by dissolving appropriate lipid(s) (such as stearoyl phosphatidyl ethanolamine, stearoyl phosphatidyl chloine, arachadoyl phosphatidyl choline, and cholesterol) in an inorganic solvent that is then evaporated, leaving behind a thin film of dried lipid on the surface of the container. An aqueous solution of the active compound (e.g., CS-87, CS-87 monophosphate, CS-87 diphosphate, and/or CS-87 triphosphate) is then introduced into the container. The container is then swirled by hand to free lipid material from the sides of the container and to disperse lipid aggregates, thereby forming the liposomal suspension.

The phosphate compounds of the present invention are prepared by phosphorylation of CS-87, as described below.

The monophosphate can be prepared according to the procedure of Imai et al., J. Org. Chem., 34(6), 1547–1550 (June 1969). For example, about 100 mg of CS-87 and about 280 $\mu$l of phosphoryl chloride are reacted with stirring in about 8 ml of dry ethyl acetate at about 0° C. for about four hours. The reaction is quenched with ice. The aqueous phase is purified on an activated charcoal column, eluting with 5% ammonium hydroxide in a 1:1 mixture of ethanol and water. Evaporation of the eluant gives 100 mg of 3'-azido-2',3'-dideoxyuridine monophosphate, as the ammonium salt.

The diphosphate can be prepared according to the procedure of Davisson et al., J. Org. Chem., 52(9), 1794–1801 (1987). 3'-Azido-2',3'-dideoxyuridine diphosphate is prepared from the tosylate of CS-87, which may be prepared, for example, by reaction CS-87 with tosyl chloride in pyridine at room temperature for about 24 hours, working up the product in the usual manner (e.g., by washing, drying, and crystallizing it).

The triphosphate can be prepared according to the procedure of Hoard et al., J. Am. Chem. Soc., 87(8), 1785–1788 (1965). For example, 3'-azido-2',3'-dideoxyuridine monophosphate is activated (by making a imidazolide, according to methods known to those skilled in the art) and treated with tributyl ammonium pyrophosphate in DMF. The reaction gives primarily 3'-azido-2',3'-dideoxyuridine triphosphate, with some unreacted monophosphate and some diphosphate. Purification by anion exchange chromatography of a DEAE column is followed by isolation of CS-87 triphosphate, e.g., as the tetrasodium salt.

Structurally related analogues such as phosphorylated and acylated derivatives of CS-87, and the uridine and C-nucleoside derivatives thereof will have similar activities at generally the same in vivo concentration ranges.

The invention now being generally described, the same will be better understood by reference to certain specific examples which are included herein for purposes of illustration only and are not intended to be limiting of the invention or any embodiment thereof, unless specified.

Various experiments were conducted to show the effects of CS-87 on the growth of certain cells, the effects of CS-87 when administered in vivo, and the effects of CS-87 on HIV replication.

The Effect of CS-87 on Cell Growth

Figure 2A:
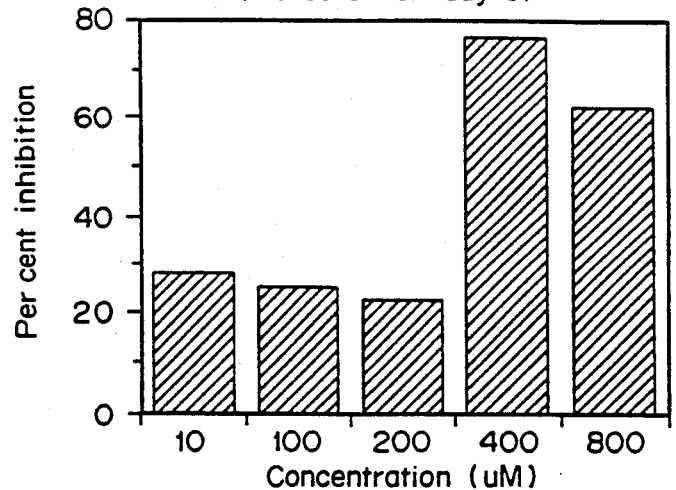
FIG. 2 shows the effects of CS-87 on the growth of (a) Vero cells and (b) human blood peripheral mononuclear (PBM) cells.
Figure 2B:
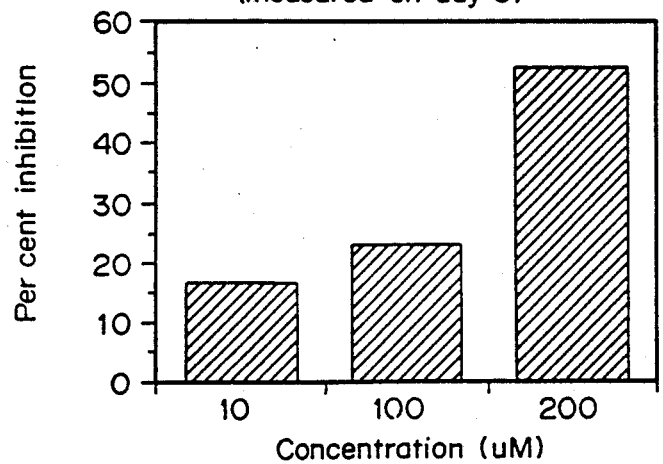

The effect of CS-87 on colony formation of human granulocytes-macrophage precursor cells was compared with the effects of AZT and CS-85 in FIG. 1. The effect of CS-87 on Vero cells is shown in FIG. 2a. Vero cells are very fast growing cells, and it can be seen from FIG. 2a that up to a concentration of about 400 micromolar, there is relatively little toxicity to these cells. PBM cells are somewhat more sensitive to CS-87 than the Vero cells, but these cells will still tolerate a concentration of CS-87 of up to about 200 micromolar before significant inhibition is noted (see FIG. 2b).

Effect of CS-87 on Animals

Figure 3:
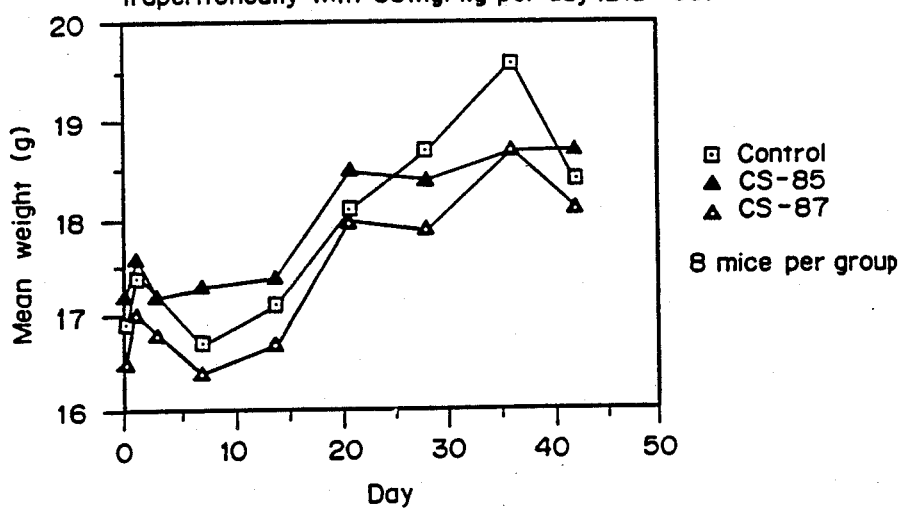
FIG. 3 is a graph showing the effect of CS-85 and CS-87 on the weight of BALB/c mice.

FIG. 3 shows the effect of CS-85 and CS-87 on the weight of uninfected BALB/c mice. It can be seen that there is no significant difference between CS-87, CS-85, and the control. The hematologic values of NIH Swiss mice treated with AZT and CS-87 (administered orally at 0.5 mg/ml ad libitum for a total of 67 days) is shown in Table 1. The significantly less toxicity of Cs-87 as compared to AZT is apparent from the differences in the RBC and MCV values.

Figure 4A:
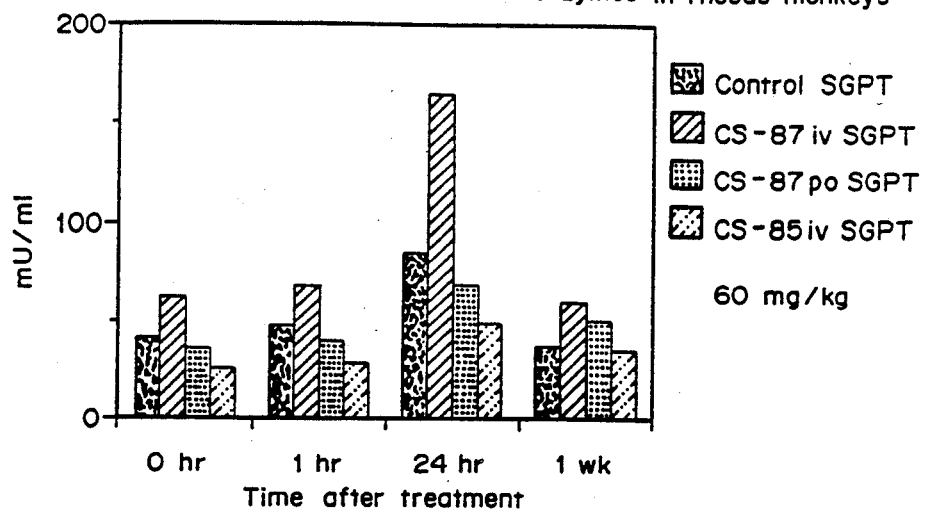
FIG. 4 shows the effects of CS-85 and CS-87 on liver enzymes (a) SGPT and (b) SGOT in rhesus monkeys. SGPT refers to Serum Glutamic Pyruvic Transaminase. SGOT refers to Oxalacetic Transaminase.
Figure 4B:
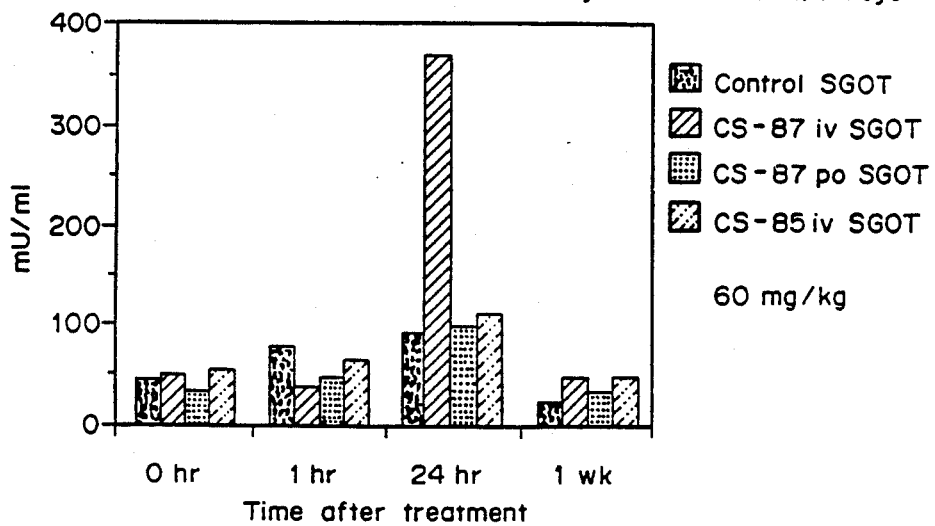

As can be seen in FIG. 4, there was a transient elevation in monkeys of SGPT and SGOT with intravenous administration of CS-87. However, the animals were back to normal after one week. It can be seen in FIG. 4 that oral administration (po) is less toxic than intravenous administration.

The pharmockinetics (serum and brain levels) of CS-87 in adult mice is shown in Table 2. In rhesus monkeys, the pharmocokinetic parameters after an oral dose of 920 mg of CS-87 are as follows:
elimination $t_{1/2}k = 0.48$ h
clearance = 1.74 L/h/kg
AUC = 113.43 mg h/L
volume of distribution $(V_{ss}) = 1.2$ L/kg
absorption rate constant $(k_a) = 1.73$ h$^{-1}$
absorption rate $t_{1/2} = 0.40$ h
elimination rate constant, $k = 1.43$ h$^{-1}$

Effect of CS-87 on the Replication of HIV in Different Types of Cells

CS-87 has selective anti-HIV-1 activity in human peripheral blood mononuclear (PBM) cells, as shown by Table 3 in combination with the foregoing data.

Since the antiviral activity of nucleoside analogs may depend on the type of assay and cell type used, the activity of CS-87 was determined in various HIV-1 susceptible cells. In addition to PBM cells, ATH-8 and the recently described HeLa-T4 cells (Cell 47: 333, 1986) were used. The median effective dose (EC$_5$O) or minimum inhibitory concentration (MIC) of CS-87 relative to 3'azido-3'-deoxythymidine (AZT) and 2',3'-dideoxycytidine (d2C) is described in Table 4.

Figure 5:
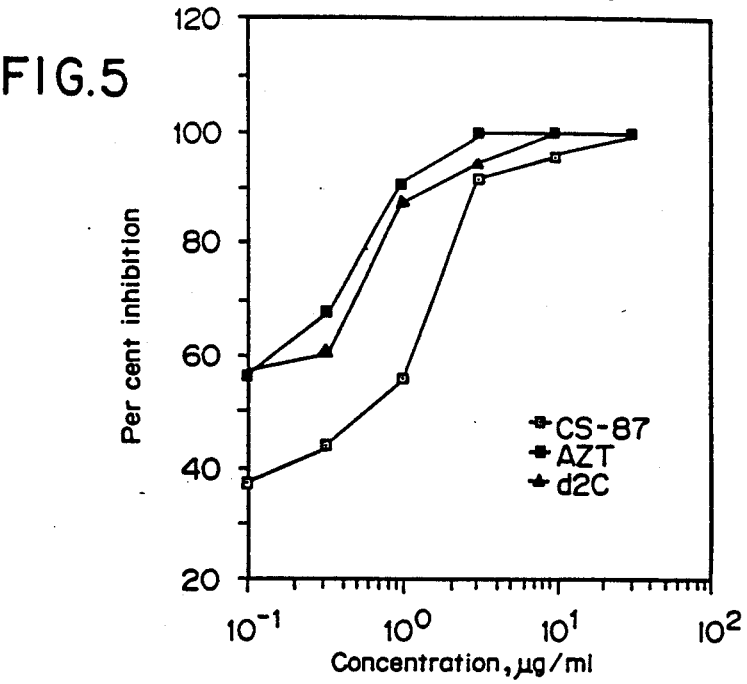
FIG. 5 compares the effect of CS-87, AZT and d2C (2',3'-dideoxycytidine) against HIV-1 (Strain RFII) in HeLa-T4 cells, percent inhibition versus concentration.

The results indicate that the potency of CS-87 and related compounds varied according to the cell system used. Although CS-87 had comparable activity to d2C in ATH-8 cells, it was less active in HeLa-T4 and PBM cells. CS-87 was not toxic to the uninfected cells when tested up to 200 $\mu$M. The percent inhibition of CS-87, AZT, and d2C against HIV-1 (Strain RFII) in HeLa-T4 cells as a function of concentration is shown in FIG. 5.

The Effect of CS-87 on Human, Non-Human Primate, and Murine Retroviruses

Figure 6:
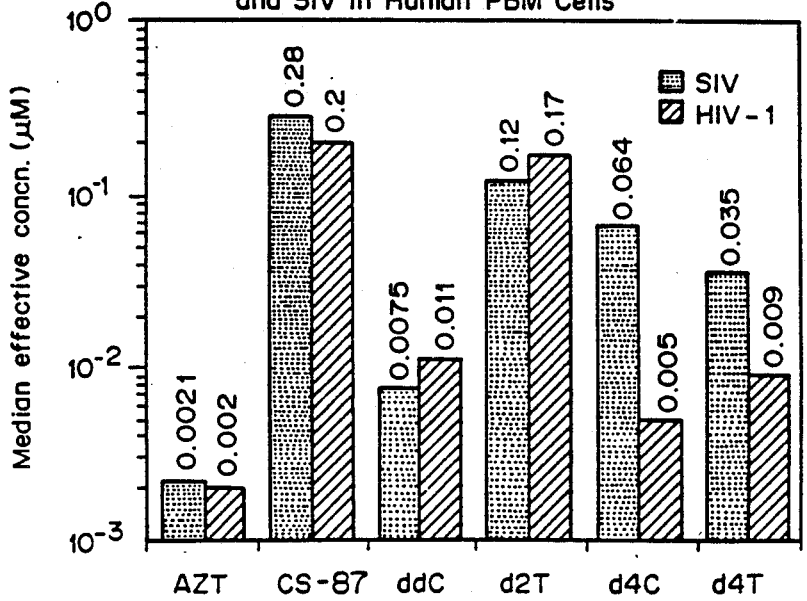
FIG. 6 is a graph of the activity of several nucleosides analogues against HIV-1 and simian immunodeficiency virus (SIV) in human PBM cells as a function of median effective concentration.

A comparison of the differences in median effective an tiviral concentrations between human, non-human primate, and murine retroviruses is shown in Table 5. CS-87 is much more effective against HIV (LAV-1) and SIV (SMM) than against Friend (EY-10) or Mouse ecotropic (Cas-Br-M virus). A further comparison of the activity of several nucleoside analogues, including CS-87, against HIV-1 and SIV in human PBM cells is shown in FIG. 6. The effect of delayed treatment with AZT, CS-87 or CS-91 on the replication of HIV-1 and SIV in human PBM cells is shown in FIGS. 7a, b, and c. It is apparent that the time of administration is critical to the effectiveness of the treatment.

Table 6 shows the effect of the 5'-triphosphates of CS-87 and AZT on HIV reverse transcriptase and alpha DNA polymerase, again demonstrating the extreme selectivity of the CS-87 compound against HIV and not the host cell $\alpha$-DNA polymerase activity).

Modifications and variations of the present invention, compositions for the treatment of HIV including 3'-azido-2',3'-dideoxyuridine and derivatives thereof, will be obvious to those skilled in the art from the foregoing detailed description of the invention. Such modifications and variations are intended to come within the scope of the appended claims.

TABLE 1

HEMATOLOGIC VALUES OF NIH SWISS MICE TREATED WITH AZT AND CS-87

| Mouse Code | Treatment | WBC × 10$^3$ | RBC × 10$^6$ | Hgb g/dL | Hct % | MCV fL | MCH pg | MCHC g/dL | RDW % | PLT × 10$^6$ |
|---|---|---|---|---|---|---|---|---|---|---|
| A | None | 6.0 | 8.1 | 13.5 | 39.5 | 48.9 | 16.7 | 34.2 | 38.6 | 1.000 |
| I | None | 6.5 | 7.9 | 12.9 | 37.1 | 46.8 | 16.3 | 34.8 | 36.2 | 1.059 |
| J | None | 8.2 | 8.6 | 14.0 | 41.4 | 48.4 | 16.4 | 33.8 | 35.7 | 1.323 |
| M | None | 6.7 | 7.5 | 11.9 | 35.1 | 47.1 | 16.0 | 33.9 | 36.5 | 0.954 |
| N | None | 7.4 | 7.3 | 12.0 | 36.0 | 49.1 | 16.4 | 33.3 | 37.1 | 1.014 |
|   | Mean | 7.0 | 7.9 | 12.9 | 37.8 | 48.1 | 16.4 | 34.0 | 36.8 | 1.1 |
|   | SD | 0.9 | 0.5 | 0.9 | 2.6 | 1.1 | 0.3 | 0.6 | 1.1 | 0.1 |
| D | AzT | 4.5 | 4.1 | 9.1 | 28.4 | 68.9 | 22.1 | 32.1 | 29.9 | 1.076 |
| C | Azt | 5.2 | 3.4 | 6.9 | 21.1 | 62.9 | 20.5 | 32.6 | 24.6 | 1.187 |
| O | AzT | 8.8 | 5.2 | 11.0 | 35.0 | 67.4 | 21.2 | 31.4 | 17.8 | 1.292 |
| P | Azt | 7.9 | 4.4 | 9.6 | 30.1 | 67.8 | 21.6 | 31.9 | 21.3 | 1.112 |
|   | Mean | 6.6 | 4.3 | 9.2 | 28.7 | 66.8 | 21.4 | 32.0 | 23.4 | 1.2 |
|   | SD | 2.1 | 0.8 | 1.7 | 5.8 | 2.6 | 0.7 | 0.5 | 5.1 | 0.1 |
| K | CS-87 | 2.6 | 7.6 | 12.9 | 37.2 | 48.8 | 16.9 | 34.6 | 34.3 | 1.158 |
| L | CS-87 | 8.9 | 8.6 | 14.1 | 44.4 | 51.7 | 16.4 | 31.8 | 16.8 | 1.35 |

TABLE 1-continued
HEMATOLOGIC VALUES OF NIH SWISS MICE TREATED WITH AZT AND CS-87

| Mouse Code | Treatment | WBC × $10^3$ | RBC × $10^6$ | Hgb g/dL | Hct % | MCV fL | MCH pg | MCHC g/dL | RDW % | PLT × $10^6$ |
|---|---|---|---|---|---|---|---|---|---|---|
| Q | CS-87 | 7.9 | 8.6 | 14.2 | 42.3 | 49.4 | 16.6 | 33.5 | 37.7 | 1.305 |
| R | CS-87 | 12.6 | 8.8 | 14.8 | 45.7 | 51.8 | 16.8 | 32.4 | 15.3 | 1.361 |
|  | Mean | 8.0 | 8.4 | 14.0 | 42.4 | 50.4 | 16.7 | 33.1 | 26.0 | 1.3 |
|  | SD | 4.1 | 0.5 | 0.8 | 3.7 | 1.6 | 0.2 | 1.2 | 11.6 | 0.1 |

AzT or CS-87 given orally at 0.5 mg/ml ad libitum for a total of 67 days.
Drug was delivered via mother for 28 days and then directly via water for 39 days
Treatment initiated on day of birth. Mice bled on day 67.

TABLE 5
Differences in Median Effective Antiviral Concentrations Between Human, Non-Human Primate, and Murine Retroviruses

| | HIV (LAV-1) | SIV (SMM) | Friend (EY-10) | Mouse ecotropic (Cas-Br-M) |
|---|---|---|---|---|
| | \multicolumn{4}{c}{$EC_{50}$ (μM)} | | | |
| AZT | 0.002 | 0.002 | 0.004 | 0.007 |
| CS-87 | 0.28 | 0.20 | >10 | 9.10 |
| CS-91 | 0.39 | 1.16 | ND | 77.9 |
| HS-20 | 2.40 | 0.52 | 0.89 | 0.79 |
| HS-21 | 3.20 | 2.30 | 0.70 | 1.16 |

TABLE 2
PRELIMINARY SINGLE DOSE PHARMACOKINETICS OF CS-87 IN ADULT MICE[a]

| Time after treatment (min.) | Serum levels (μg/ml) | Brain levels (μg/ml) | Ratio: % B/S |
|---|---|---|---|
| 5 | 71.3 | 3.10 | 4.3 |
| 5 | 125.7 | 7.86 | 6.3 |
| 31 | 91.0 | 11.11 | 12.2 |
| 34 | 55.5 | 5.67 | 10.2 |
| 71 | 24.5 | 6.40 | 26.1 |
| 72 | 54.8 | 7.33 | 13.4 |

[a]Mice were administered the drug at a dose of 250 mg/kg iv.

TABLE 4-continued
SUMMARY OF ANTIVIRAL ACTIVITY AGAINST HIV-1 OF CS-87, AZT AND D2C IN VARIOUS CELL SYSTEMS

| Treatment | PBM ($EC_{50}$) | HeLa-T4 ($EC_{50}$) | ATH-8 (MIC) |
|---|---|---|---|
| d2C (ddC) | 0.011 | 0.48 | 0.47 |

TABLE 6
EFFECT OF THE 5'-TRIPHOSPHATES OF CS-87 AND AZT ON HIV REVERSE TRANSCRIPTASE AND ALPHA DNA POLYMERASE

| Compound | HIV RT $K_1$, nM | Host cell α-DNA pol $K_1$, nM | Ratio: Cellular/HIV |
|---|---|---|---|
| CS-87-TP | 9 | 1.2 | 133,333 |
| AZT-TP | 40[a] | 0.23[a] | 5,750 |

[a]According to Furman et al. Proc.Natl.Acad.Sci.1986.

We claim:
1. A method for treating HIV in a human, which method comprises administering a compound having the formula:

TABLE 3
EFFECT OF VARIOUS DRUGS ON THE REPLICATION OF HIV IN HUMAN PERIPHERAL BLOOD MONONUCLEAR CELLS
(Reverse transcriptase assay, p24 RIA, and western blot analysis)

| Treatment | Concn. (μM) | RT: Mean DPM/ml on day 5 (3 day old cells) | % Inhibition (corrected) | RIA p24 ng/ml (Dupont kit) | % Inhibition | Western blot* p24 | p41 |
|---|---|---|---|---|---|---|---|
| Control (virus only) |  | 637,826 | 0.0 | 24.08 | 0.0 | 3+ | 2+ |
| AZT | 0.01 | 65,208 | 89.8 | 4.39 | 81.8 | 2+ | 1+ |
|  | 0.1 | 6,144 | 99.1 | 0.51 | 97.9 | 0 | 0 |
|  | 1 | 2,304 | 99.7 | 0.18 | 99.3 | 0 | 0 |
| CS-87 | 0.1 | 367,934 | 42.3 | 21.86 | 9.2 | 3+ | 2+ |
|  | 1 | 188,878 | 70.4 | 11.76 | 51.2 | 2+ | 1+ |
|  | 10 | 12,904 | 98.0 | 0.65 | 97.3 | 0 | 0 |
| No virus/no drug |  | 5,326 |  | 0.01 |  | 0 | 0 |
| Control for RT |  | 336,432 |  |  |  |  |  |
| H9 marker |  |  |  |  |  | 4+ | 2+ |
| Blank |  | 370 |  |  |  |  |  |

*Western blot (band intensity):
0 = none;
1+ = weak;
2+ = moderate;
3+ = strong;
4+ = very strong.

TABLE 4
SUMMARY OF ANTIVIRAL ACTIVITY AGAINST HIV-1 OF CS-87, AZT AND D2C IN VARIOUS CELL SYSTEMS

| Treatment | PBM ($EC_{50}$) | HeLa-T4 ($EC_{50}$) | ATH-8 (MIC) |
|---|---|---|---|
| CS-87 | 0.18 | 1.24 | 0.40 |
| AZT | 0.002 | 0.34 | 0.32 |

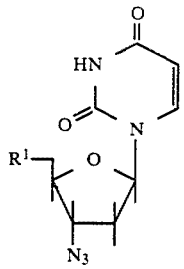

wherein R¹ is OH monophosphate, diphosphate, triphosphate; or a pharmacologically acceptable salt thereof, in association with a pharmaceutically acceptable carrier; to a human being infected by HIV, in an amount effective for the treatment of an HIV infection.

2. The method of claim 1, wherein said compound is protected against rapid elimination from the body.

3. The method of claim 1, wherein said pharmaceutically acceptable carrier comprises a liposomal suspension.

4. The method of claim 3, wherein R¹ is monophosphate, diphosphate, or triphosphate.

5. The method of claim 1, wherein R¹ is monophosphate, diphosphate, or triphosphate.

6. The method of claim 1, wherein R¹ is OH.

* * * * *